(12) United States Patent
Mahajan

(10) Patent No.: US 7,202,396 B2
(45) Date of Patent: Apr. 10, 2007

(54) RAD3 ORTHOLOGUES AND USES THEROF

(75) Inventor: Pramod B. Mahajan, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 896 days.

(21) Appl. No.: 10/378,018

(22) Filed: Feb. 28, 2003

(65) Prior Publication Data

US 2003/0167530 A1  Sep. 4, 2003

Related U.S. Application Data

(62) Division of application No. 09/735,101, filed on Dec. 12, 2000, now Pat. No. 6,559,355.

(60) Provisional application No. 60/170,597, filed on Dec. 13, 1999.

(51) Int. Cl.
*C12N 15/29* (2006.01)
*C12N 15/52* (2006.01)
*C12N 15/63* (2006.01)
*C12N 15/82* (2006.01)
*A01H 1/00* (2006.01)

(52) U.S. Cl. .......................... 800/278; 435/6; 435/69.1; 435/320.1; 435/419; 435/468; 536/23.1; 536/23.2; 536/23.6; 800/281; 800/298

(58) Field of Classification Search ................ 800/278, 800/281, 298; 435/6, 69.1, 320.1, 468, 419; 536/23.1, 23.2, 23.6
See application file for complete search history.

(56) References Cited

U.S. PATENT DOCUMENTS

| 5,500,365 A | 3/1996 | Fischhoff et al. |
| 6,747,137 B1 * | 2/1998 | Weinstock et al. |

FOREIGN PATENT DOCUMENTS

WO  WO 99/41394 A1  8/1999

OTHER PUBLICATIONS

DNA Sequence Search, USPTO, Apr. 29, 2002.
Bailis et al., The Essential Helicase Gene RAD3 Suppresses Short-Sequence Recombination in Saccharomyces cerevisiae, Mol. Cell. Biol. 15(8):3998-4008 (1995).
Bailly et al., DNA-RNA helicase activity of RAD3 protein of Saccharomyces cerevisiae, Proc. Natl. Acad. Sci. USA 88:9712-9716 (1991).
Bardwell et al., Yeast RAD3 protein binds directly to both SSL2 and SSL1 proteins: Implications for the structure and function of transcription/repair factor b, Proc. Natl. Acad. Sci. USA 91:3926-3930 (1994).
Brandriff et al., Human Chromosome 19p: A Fluorescence in Situ Hybridization Map with Genomic Distance Estimates for 79 Intervals Spanning 20 Mb, Genomics 23:582-591 (1994).
Brodsky et al., GenBank Accession No. AF132140, Full Length Drosophila melanogaster cDNA sequence (1999).
Davies et al., Isolation of Arabidopsis thaliana mutants hypersensitive to gamma radiation, Mol. Gen. Genet. 243:660-665 (1994).
de Boer et al., Disruption of the Mouse Xeroderma Pigmentosum Group D DNA Repair/Basal Transcription Gene Results in Preimplantation Lethality, Cancer Research 58:89-94 (1998).
Feaver et al., Dual Roles of Multiprotein Complex from S. cerevisiae in Transcription and DNA Repair, Cell 75:1379-1387 (1993).
Friedberg et al., DNA Repair and Mutagenesis, Chapters 6 & 7, pp. 233-316, ASM Press, Washington, DC (1995).
Guzder et al., DNA repair gene RAD3 of S. cerevisiae is essential for transcription by RNA polymerase II, Nature 367:91-94 (1994).
Lewin, B., Genes V, Oxford Universtiy Press, New York, pp. 264-265 (1994).
Montelone et al., Spontaneous Mitotic Recombination in Yeast: The Hyper-Recombinational rem1 Mutations Are Alleles of the RAD3 Gene, Genetics 119:289-301 (1988).
Montelone et al., Analysis of the rad3-101 and rad3-102 Mutations of Saccharomyces cerevisiae: Implications for Structure/Function of Rad3 Protein, Yeast 10:13-17 (1994).
Murray et al., Cloning and characterisation of the S.pombe rad15 gene, a homolgue to the S.cerevisiae RAD3 and human ERCC2 genes, Nuc. Acids Res. 20(11):2673-2678 (1992).
Naegeli et al., Substrate Specificity of the Rad3 ATPase/DNA Helicase of Saccharomyces cerevisiae and Binding of Rad3 Protein to Nucleic Acids, J. Biol. Chem. 267(11):7839-7844 (1992).
Nam et al., Agrobacterium tumefaciens Transformation of the Radiation Hypersensitive Arabidopsis thaliana Mutants uvh1 and rad5, MPMI 11(11):1136-1141 (1998).
Naumovski et al., Molecular Cloning of Eucaryotic Genes Required for Excision Repair of UV-Irradiated DNA: Isolation and Partial Characterization of the RAD3 Gene of Saccharomyces cerevisiae, J. Bacteriol. 152(1):323-331 (1982).
Naumovksi et al., A DNA repair gene required for the incision of damaged DNA is essential for viability in Saccharomyces cerevisiae, Proc. Natl. Acad. Sci. USA 80:4818-4821 (1983).
Reynolds et al., The nucleotide sequence of the RAD3 gene of Saccharomyces cerevisiae: a potential ademine nucleotide binding amino acid sequence and a nonessential acidic carboxyl terminal region, Nucleic Acids Res. 13(7)2357-2372 (1985).
Reynolds et al., The Schizosaccharomyces pombe rhp3+ gene required for DNA repair and cell viability is functionally interchangeable with the RAD3 gene of Saccharomyces cerevisiae, Nucleic Acids Res. 20(9):2327-2334 (1992).
Siede, W., DNA Damage and Repair, vol. I, Part II, pp. 307-333, Ed. Nickoloff, J.A. and Hoekstra, M.F., Humana Press, Totowa, NJ (1998).

(Continued)

Primary Examiner—Phuong Bui
Assistant Examiner—Brendan O. Baggot

(57) ABSTRACT

The invention provides isolated Rad3 nucleic acids and their encoded proteins. The present invention provides methods and compositions relating to pyrimidine excision activity, altering Rad3 levels in plants, increasing transformation efficiency, or creating male sterile plants or seedless fruits. The invention further provides recombinant expression cassettes, host cells, transgenic plants, and antibody compositions.

6 Claims, No Drawings

OTHER PUBLICATIONS

Song et al., Effects of Multiple Yeast rad3 Mutant Alleles on UV Sensitivity, Mutability, and Mitotic Recombination, J. Bacteriol. 172(12):6620-6630 (1990).

Sung et al., The RAD3 gene of Saccharomyces cerevisiae encodes a DNA-dependent ATPase, Proc. Natl. Acad. Sci. USA 84:6045-6049 (1987).

Sung et al., RAD3 protein of Saccharomyces cerevisiae is a DNA helicase, Proc. Natl. Acad. Sci. USA 84:8951-8955 (1987).

Sung et al., Mutation of lysine-48 to arginine in the yeast RAD3 protein abolishes its ATPase and DNA helicase activities but not the ability to bind ATP, EMBO J. 7(10):3263-3269 (1988).

Sung et al., Human xeroderma pigmentosum group D gene encodes a DNA helicase, Nature 365:852-855 (1993).

Sung et al., Nagative Superhelicity Promotes ATP-dependent Binding of Yeast RAD3 Protein to Ultraviolet-damaged DNA, J. Biol. Chem. 269(11):8303-8308 (1994).

Sung et al., Reconstitution of TFIIH and Requirement of Its DNA Helicase Subunits, Rad3 and Rad25, in the Incision Step of Nucleotide Excision Repair, J. Biol. Chem. 271(18)10821-10826 (1996).

Vonarx et al., GenBank Accession No. AF188623, A Rad3/XP-D/ERCC2 homolog from Arabidopsis thaliana (1999).

Vysotskaia et al., GenBank Accession No. AC005278 Arabidopsis thaliana chromosome 1 BAC F15K9 sequence (1998).

Walbot V., EST GenBank Accession No. AI600918, Maize ESTs from various cDNA libraries sequenced at Stanford University (1999).

Walbot V., EST GenBank Accession No. AI833934, Maize ESTs from various cDNA libraries sequenced at Stanford Univerity (1999).

Walter et al., Linkage Assignment of a DNA Sequence (ERCC2L1) Homologous to a Human DNA Repair Gene in Xiphophorus Fishes: Implications for the Evolutionary Derivation of Human Chromosome 19, Genomics 10:1083-1086 (1991).

Weber et al., Molecular analysis of CXPD mutations in the repair-deficient hamster mutants UV5 and UVL-13, Mutation Research 324:147-152 (1994).

Yang et al., A Mutation in a Saccharomyces cerevisiae Gene (RAD3) Required for Nucleotide Excision Repair and Transcription Increases the Efficiency of Mismatch Correction, Genetics 144:450-466 (1996).

* cited by examiner

RAD3 ORTHOLOGUES AND USES THEROF

CROSS-REFERENCE TO RELATED APPLICATIONS

This application is a divisional of U.S. application Ser. No. 09/735,101 filed Dec. 12, 2000 now U.S. Pat. No. 6,559,355, and claims the benefit of U.S. application Ser. No. 60/170,597 filed Dec. 13, 1999, now abandoned, which are all herein incorporated in entirety by reference.

TECHNICAL FIELD

The present invention relates generally to plant molecular biology. More specifically, it relates to nucleic acids and methods for modulating their expression in plants.

BACKGROUND OF THE INVENTION

In the yeast *Saccharomyces cerevisiae*, the RAD3 gene is required for the excision of pyrimidine dimers formed in UV-damaged DNA (Freidberg, E. et al., in "DNA repair and Mutagenesis" pp. 233–316, ASM Press Washington, D.C., 1995; Siede, W. in "DNA Damage and Repair Vol. 2 " pp. 307–333, Ed. Nickoloff J. A. and Hoekstra M. F., Humana Press, Totowa, N.J., 1998). In addition to the involvement of RAD3 in excision repair, the yeast RAD3 gene is also essential for cell viability (Freidberg, E. et al., in "DNA repair and Mutagenesis" pp. 233–316, ASM Press Washington, D.C., 1995; Siede, W. in "DNA Damage and Repair Vol. 1, Part II" pp. 307–333, Ed. Nickoloff J. A. and Hoekstra M. F., Humana Press, Totowa, N.J., 1998). The RAD3 gene encodes a protein, Rad3, consisting of 778 amino acids (~90 kDa) and having 20 predominantly acidic amino acids at the carboxyl terminus. Deletions of this acidic region have no obvious effect on cell viability or DNA repair (Reynolds, et al., *Nucleic Acid Res.* 13: 2357–2372, 1985).

The yeast Rad3 protein is a single stranded DNA dependent ATPase (Sung, P. et al., *Proc. Nat. Aced. Sci.* 84:6045–6049, 1987). It is also an ATP-dependent DNA helicase with 5'–3' specificity (Sung, P. et al., *Proc. Nat. Aced. Sci.* 84:8951–8955, 1987). Purified yeast Rad3 catalyzes the displacement of RNA fragments annealed to complementary DNA and possesses a potent helicase activity against DNA:RNA hybrid duplexes. The ATP-hydrolysis reaction is not affected by ribonucleotide homopolymers (Bailly V. et al., *Proc. Nat. Aced. Sci.* 88:9712–9716, 1991; Naegeli, H. et al., *J. Biol. Chem.* 267:7839–7844, 1992). Purified Rad3 exhibits preferential binding to UV-damaged DNA over non-damaged DNA. This binding is dependent on ATP hydrolysis and is promoted by negative superhelicity (Sung, P. et al., *J. Biol. Chem.* 269:8303–8308, 1994).

Recently, Guzder et al. showed an involvement of the yeast RAD3 gene in transcription by RNA polymerase II (Guzder, S. et al., *Nature* 367:91–94, 1994). Biochemical and genetic analysis has shown that Rad3 is an authentic subunit of transcription factor b or Tfb, also known as transcription Factor IIH or TFIIH (Feaver W J et al., *Cell* 7:1379–1387, 1993; Bardwell, L. et al., *Proc. Natl. Aced. Sci.* 91:3926–3930, 1994). Further in vitro reconstitution studies using recombinant proteins have established that the helicase activity of Rad3 and other TFIIH subunits are required for the incision step of nucleotide excision repair (Sung, P. et al., *J. Biol. Chem.* 271:10821–10826, 1996).

Systematic biochemical and genetic analyses of various mutants has allowed for the dissection of multiple functions of yeast Rad3. For example, mutation of yeast Rad3 at lysine-48 to arginine abolishes its ATPase and helicase activity but has no effect on the ability of the protein to bind ATP (Sung, P. et al., *EMBO J.* 7:3363–3369, 1988.) Mutations in RAD3 have also resulted in mitotic hyper-recombination without affecting the UV-sensitivity. These rem-1 and rem-2 mutations (for recombination/mutation) have been mapped to codons 237 and 661 (Montelone, B. et al., *Genet.* 119:289–301, 1988; Song, J M et al., *J. Bacteriol.* 172:6620–6630, 1990; Montelone B A and Malone R E, *Yeast* 10:13–27, 1994). Another RAD3 mutant (Gly-595 Arg) shows elevated levels of recombination between sequences shorter than 300 bp (Bailis, A et al., *Mol. Cell. Biol.* 15:3998–4008,1995). Finally, the rad3-1 allele has recently been shown to increase the efficiency of mismatch repair (Yang, Y. et al., *Genet.* 144:459–466, 1996).

Homologues of the *S. cerevisiae* RAD3 gene have been cloned from *Schizosaccharomyces pombe*, human, hamster, fish, and mouse (Reynolds P R et al., *Nucleic Acid Res.* 20:2327–2334,1992; Murray J M et al., *Nucleic Acids Res.* 20:2673–2678, 1992; Sung P et al., *Nature* 365:852–855, 1993; Weber Calif. et al., *Mutat. Res.* 324:147–152, 1993; Kirchner J M et al., *Genomics* 23:592–599, 1994; Walter R B et al., *Genomics* 10: 1083–1086, 1991; de Boer J et al., *Cancer Res.* 58:89–94, 1998). Recently, a *Drosophila melanogaster* sequence (Accession Number AF132140) and an *Arabidopsis thaliana* sequence (Accession Number AC005278) both showing similarity to RAD3 have been deposited in Genbank. The present invention describes a full-length cDNA sequence which encodes the maize orthologue of RAD3.

The modulation of Rad3 will provide for many advantages. One advantage involves the regulation of DNA repair and recombination. Enhancing DNA repair and DNA recombination will increase the efficiency with which heterologous nucleic acids are incorporated into the genomes of a target plant cell. Control of these processes has important implications in the creation of novel recombinantly engineered crops such as maize or soybean.

Another advantage to the modulation of Rad3 involves cell viability. RAD3 mutants have been found to be lethal in haploid cells (Naumovski, L., and E. C. Friedberg, *Proc. Natl. Acad. Sci.* 80:4818–4821, 1983). Thus, by reducing Rad3 levels in anther cells, development may cease, which may lead to a male sterile phenotype. Alternatively, if Rad3 expression in cell culture is modulated by the use of an inducible promoter, cell growth may be induced, thereby improving transformation. The present invention provides for these and other advantages.

SUMMARY OF THE INVENTION

Rad3 is a DNA repair enzyme shown to be important for cell viability in yeast. The present invention provides nucleic acids and proteins relating to Rad3. The present invention also provides transgenic plants comprising the nucleic acids of the present invention, and methods for modulating, in a transgenic plant, the expression of the nucleic acids of the present invention. In particular, the polynucleotides and polypeptides of the present invention can be expressed temporally or spatially, e.g., at developmental stages, in tissues, and/or in quantities, which are uncharacteristic of non-recombinantly engineered plants. This invention provides utility in such exemplary applications as modulating DNA repair to increase transformation efficiency and modulating levels of Rad3 in tissues, such as anthers, in order to create male sterile plants.

DETAILED DESCRIPTION OF THE INVENTION

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology. Principles and Applications*, D. H. Persing et al., Ed., American Society for Microbiology, Washington, D.C (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells, excluding human cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" and "polynucleotide" are used interchangably and includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

Unless otherwise stated, the term "Rad3 nucleic acid" is a nucleic acid of the present invention and means a nucleic acid comprising a polynucleotide, or a fragment thereof, encoding a Rad3 polypeptide or a useful fragment thereof. A "maize Rad3 gene" is a gene of the present invention and refers to a heterologous genomic form of a full-length maize Rad3 polynucleotide.

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The classes of plants which can be used in the methods of the invention include both monocotyledonous and dicotyledonous plants. A particularly preferred plant is *Zea mays*.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "Rad3 polypeptide" is a polypeptide of the present invention with DNA repair activity and refers to one or more amino acid sequences, in glycosylated or non-glycosylated form. The term is also inclusive of fragments, variants, homologs, alleles or precursors (e.g., preproproteins or proproteins) thereof. For the purpose of this description, the terms "polypeptide" and "protein" are used interchangably.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with $\geq 90\%$ identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, CABIOS 5: 151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., Eds., Greene Publishing and Wiley-Interscience, New York (1995).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5877, 1993). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149–163, 1993) and XNU (Clayerie and States, *Comput. Chem.,* 17:191–201, 1993) low-complexity filters can be employed alone or in combination.

GAP can also be used to compare a polynucleotide or polypeptide of the present invention with a reference sequence. GAP uses the algorithm of Needleman and Wunsch (*J. Mol. Biol.* 48:443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each independently be: 0, 1, 2, 3, 4, 5, 6, 7, 8, 9, 10, 15, 20, 30, 40, 50, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters (Altschul et al., *Nucleic Acids Res.* 25:3389–3402, 1997; Altschul et al., J. Mol. Bio. 215:403–410,1990) or to the value obtained using the GAP program using default parameters (see the Wisconsin Genetics Software Package, Genetics Computer Group (GCG), 575 Science Dr., Madison, Wis., USA).

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Overview

In addition to its role in repairing damages to DNA, mutational analyses of Rad3 have demonstrated many other activities related to DNA binding, unwinding, and recombination activities. These functions could prove to be very useful for improving plant transformation. For example, independent of tissue type, the efficiency of transformation could be improved if one improved recombination frequency. The latter could be achieved by over-expression of Rad3. Rad3 is also critical for cell viability, and Rad3 mutants can be lethal in haploid cells. Therefore, by reducing the levels of Rad3 in haploid cells, one could alter development of specific tissues, which may lead to a male sterile phenotype or seedless fruits. Control of these processes has important implications in the creation of novel recombinantly engineered crops such as maize.

For the reasons stated above, having new Rad3 homologues would be highly desirable. A nucleotide excision repair protein XP-D homologue from *Arabidopsis* has been deposited into GenBank (Accession Number AF188623) as well an ERCC2 nucleotide excision repair homologue from *Arabidopsis* (Accession Number AC005278). There have also been GenBank deposits of two *Zea mays* ESTs of unknown function that show some similarity to Rad3 (Accession Numbers AI600918 and AI833934). The present invention describes and characterizes the first full-length cDNA for a Rad3 orthologue from a monocot plant The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provided utility in such exemplary applications as modulating transformation efficiency by regulating DNA repair and recombination and creating male sterile plants by modulating cell viability.

The present invention also provides isolated nucleic acids comprising polynucleotides of sufficient length and complementarity to a gene of the present invention to use as probes or amplification primers in the detection, quantification, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzymatic activity in screening assays of compounds, for detection of any number of allelic variants (polymorphisms), orthologues, or paralogues of the gene, or for site-directed mutagenesis in eukaryotic cells (see, e.g., U.S. Pat. No. 5,565,350). The isolated nucleic acids of the present invention can also be used for recombinant expression of their encoded polypeptides. The polypeptides can be used as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including *Hordeum, Secale, Triticum, Sorghum* (e.g., *S. bicolor*) and *Zea* (e.g., *Z. mays*). The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Glycine, Pisum, Phaseolus, Lolium, Oryza,* and *Avena*.

Nucleic Acids

Rad3 has been shown to have an extensive number of functions related to DNA repair and recombination as well as cell viability. The present invention provides, among other things, isolated nucleic acids of RNA, DNA, and analogs and/or chimeras thereof, comprising a Rad3 polynucleotide of the present invention. The nucleic acids of the present invention can be obtained form various organisms, including plants and in particular monocots or dicots.

A polynucleotide of the present invention is inclusive of:

(a) a polynucleotide encoding a polypeptide of SEQ ID NO: 2 including exemplary polynucleotides of SEQ ID NO:1; the polynucleotide sequence of the invention also includes the maize Rad3 polynucleotide sequence as contained in the plasmid deposited with American Type Culture Collection (ATCC) assigned Accession Number PTA-786.

(b) a polynucleotide which is the product of amplification from a *Zea mays* nucleic acid library using primer pairs which selectively hybridize under stringent conditions to loci within the polynucleotide of SEQ ID NO: 1; or the sequence as contained in the ATCC deposit assigned Accession Number PTA-786.

(c) a polynucleotide which selectively hybridizes to a polynucleotide of (a) or (b);

(d) a polynucleotide having a specified sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least a specific number of contiguous nucleotides from a polynucleotide of (a), (b), (c), (d), (e) or (f).

The polynucleotide of SEQ ID NO: 1 is contained in a plasmid deposited with American Type Culture Collection (ATCC) on Sep. 24, 1999 and assigned Accession Number PTA-786. American Type Culture Collection is located at 10801 University Blvd., Manassas, Va. 20110-2209.

The ATCC deposit will be maintained under the terms of the Budapest Treaty on the International Recognition of the Deposit of Microorganisms for the Purposes of Patent Procedure. The deposit is provided as a convenience to those of skill in the art and is not an admission that a deposit is required under 35 U.S.C. Section 112. The deposited sequences, as well as the polypeptides encoded by the sequences, are incorporated herein by reference and control in the event of any conflict, such as a sequencing error, with the description in this application.

A. Polynucleotides Encoding a Polypeptide of the Present Invention

The present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of SEQ ID NO: 1, and the sequence as contained in the ATCC deposit assigned Accession Number PTA-786, and polynucleotides encoding a polypeptide of SEQ ID NO: 2.

B. Polynucleotides Amplified from a *Zea mays* Nucleic Acid Library

The present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138:171–174, 1994), Biotinylated CAP Trapper (Carninci, P., Kvan, C., et al. *Genomics* 37:327–336, 1996), and CAP Retention Procedure (Edery, E., Chu, L. L., et al. *Molecular and Cellular Biology* 15:3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and Retro- Amp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, *Techniques* 1:165 (1989).

C. Polynucleotides which Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, safflower, sunflower, alfalfa, oats, sugar cane, millet, barley, and rice. Optionally, the cDNA library comprises at least 30% to 95% full-length sequences (for example, at least 30%, 40%, 50%, 60%, 70%, 80%, 90%, or 95% full-length sequences). The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST or GAP algorithms under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 97/20078. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide The present invention provides isolated nucleic acids comprising polynucleotides of the present invention, wherein the polynucleotides encode a protein having a subsequence of contiguous amino acids from a prototype polypeptide of the present invention such as is provided in SEQ ID NO.2. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

The present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides which are Subsequences of the Polynucleotides of (A)–(F)

The present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al., *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

A1. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude *Proc. Nat. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel et al., Eds., Greene Publishing and Wiley-Interscience, New York (1995); and, Swaroop et al., *Nucl. Acids Res.*, 19(8):1954 (1991). cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook et al., *Molecular Cloning: A Laboratory Manual*, 2nd Ed., Cold Spring Harbor Laboratory Vols. 1–3 (1989), Methods in Enzymology, Vol. 152. *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *BioTechniques*, 22(3): 481–486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill. One exemplary promoter is the ubiquitin promoter, which can be used to drive expression of the present invention in maize embryos or embryogenic callus.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue.

Thus, in some embodiments, the nucleic acid construct will comprise a promoter functional in a plant cell, such as in *Zea mays,* operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook,* Chapter 116, Freeling and Walbot, Eds., Springer, N.Y. (1994). The vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth in Enzymol.,* 153:253–277 (1987).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85:8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989)111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity with a polypeptide of the present invention. The percentage of sequence identity is an integer selected from the group consisting of from 50 to 99. Exemplary sequence identity values include 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% and 99%. Sequence identity can be determined using, for example, the GAP or BLAST algorithms.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, non-human mammalian cells, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus any method which provides for effective transformation/transfection may be employed.

A. Plant Transformation

A DNA sequence coding for the desired polypeptide of the present invention, for example a cDNA or a genomic sequence encoding a full length protein, will be used to construct a recombinant expression cassette which can be introduced into the desired plant.

Isolated nucleic acids of the present invention can be introduced into plants according to techniques known in the art. Generally, recombinant expression cassettes as described above and suitable for transformation of plant cells are prepared. The isolated nucleic acids of the present invention can then be used for transformation. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) *Biotechniques* 4:320–334), electroporation (Riggs et al (1986) *Proc. Natl. Acad. Sci. USA* 83:5602–5606, *Agrobacterium* mediated transformation (U.S. Pat. Nos. 5,563,055 and 5,981,840), direct gene transfer (Paszkowski et al (1984) *EMBO J.* 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods,* Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Phisiol.* 87:671–674 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839 (maize); Hooykaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports*, 5:81–84. These plants may then be grown, and either pollinated with the same transformed strain or different strains, and the resulting plant having the desired phenotypic characteristic identified. Two or more generations may be grown to ensure that the subject phenotypic characteristic is stably maintained and inherited and then seeds harvested to ensure the desired phenotype or other property has been achieved B. Transfection of Prokaryotes, Lower Eukaryotes, and Animal Cells A vector containing the appropriate DNA sequence as described elsewhere herein, as well as an appropriate promoter, and other appropriate control sequences, may be introduced into an appropriate host using a variety of well known techniques suitable to expression therein of a desired polynucleotide or polypeptide. The host cell can be a prokaryotic cell, such as a bacterial cell, a lower eukaryotic cell, such as a yeast cell or a higher eukaryotic cell, such as a mammalian or plant cell.

Introduction of the construct into the host cell can be effected by calcium phosphate transfection, DEAE-dextran mediated transfection, microinjection, cationic lipid-mediated transfection, electroporation, transduction, ballistic introduction, infection or other methods. Such methods are described in many standard laboratory manuals, such as Davis et al., *Basic Methods in Molecular Biology*, (1986); Sambrook et al., *Molecular Cloning: A Laboratory Manual*, 2nd Ed., Cold Spring Harbor Laboratory Press, Cold Spring Harbor, N.Y. (1989); and Kuchler, R. J., *Biochemical Methods in Cell Culture and Virology*, Dowden, Hutchinson and Ross, Inc. (1977). The transfected cells are cultured by means well known in the art.

Representative examples of appropriate hosts include bacterial cells, such as *streptococci, staphylococci, E. coli, streptomyces* and *Salmonella typhimurium* cells; fungal cells, such as yeast cells and *Aspergillus* cells; insect cells such as *Drosophila* S2 and *Spodoptera* Sf9 cells; animal cells such as CHO, COS and Bowes melanoma cells; and plant cells. Hosts for a great variety of expression constructs are well known, and those of skill will be enabled by the present disclosure readily to select a host for expressing a polypeptide in accordance with this aspect of the present invention.

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology.* Vol. 2: *Special Methods in Peptide Synthesis, Part A.*; Merrifield et al., *J. Am. Chem. Soc.* 85:2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillilan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by *Agrobacterium* from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.),* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant. The method comprises introducing into a plant cell a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.- H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Computer Applications

The present invention provides machines, data structures, and processes for modeling or analyzing the polynucleotides and polypeptides of the present invention.

A. Machines and Data Structures

The present invention provides a machine having a memory comprising data representing a sequence of a polynucleotide or polypeptide of the present invention. The machine of the present invention is typically a digital computer. The memory of such a machine includes, but is not limited to, ROM, or RAM, or computer readable media such as, but not limited to, magnetic media such as computer disks or hard drives, or media such as CD-ROM. Thus, the present invention also provides a data structure comprising a sequence of a polynucleotide of the present invention embodied in a computer readable medium. As those of skill in the art will be aware, the form of memory of a machine of the present invention or the particular embodiment of the computer readable medium is not a critical element of the invention and can take a variety of forms.

B. Homology Searches

The present invention provides a process for identifying a candidate homologue (i.e., an ortholog or paralog) of a polynucleotide or polypeptide of the present invention. A candidate homologue has statistically significant probability of having the same biological function (e.g., catalyzes the same reaction, binds to homologous proteins/nucleic acids) as the reference sequence to which it's compared. Accordingly, the polynucleotides and polypeptides of the present invention have utility in identifying homologs in animals or other plant species, particularly those in the family Gramineae such as, but not limited to, sorghum, wheat, or rice.

The process of the present invention comprises obtaining data representing a polynucleotide or polypeptide test sequence. Test sequences are generally at least 25 amino acids in length or at least 50 nucleotides in length. Optionally, the test sequence can be at least 50, 100, 150, 200, 250, 300, or 400 amino acids in length. A test polynucleotide can be at least 50, 100, 200, 300, 400, or 500 nucleotides in length. Often the test sequence will be a full-length sequence. Test sequences can be obtained from a nucleic acid of an animal or plant. Optionally, the test sequence is obtained from a plant species other than maize whose function is uncertain but will be compared to the test sequence to determine sequence similarity or sequence identity; for example, such plant species can be of the family Gramineae, such as wheat, rice, or sorghum. The test sequence data are entered into a machine, typically a computer, having a memory that contains data representing a reference sequence. The reference sequence can be the sequence of a polypeptide or a polynucleotide of the present invention and is often at least 25 amino acids or 100 nucleotides in length. As those of skill in the art are aware, the greater the sequence identity/similarity between a reference sequence of known function and a test sequence, the greater the probability that the test sequence will have the same or similar function as the reference sequence.

The machine further comprises a sequence comparison means for determining the sequence identity or similarity between the test sequence and the reference sequence. Exemplary sequence comparison means are provided for in sequence analysis software discussed previously. Optionally, sequence comparison is established using the BLAST or GAP suite of programs.

The results of the comparison between the test and reference sequences can be displayed. Generally, a smallest sum probability value (P(N)) of less than 0.1, or alternatively, less than 0.01, 0.001, 0.0001, or 0.00001 using the BLAST 2.0 suite of algorithms under default parameters identifies the test sequence as a candidate homologue (i.e., an allele, ortholog, or paralog) of the reference sequence. A nucleic acid comprising a polynucleotide having the sequence of the candidate homologue can be constructed using well known library isolation, cloning, or in vitro synthetic chemistry techniques (e.g., phosphoramidite) such as those described herein. In additional embodiments, a nucleic acid comprising a polynucleotide having a sequence represented by the candidate homologue is introduced into a plant; typically, these polynucleotides are operably linked to a promoter. Confirmation of the function of the candidate homologue can be established by operably linking the candidate homolog nucleic acid to, for example, an inducible promoter, or by expressing the antisense transcript, and analyzing the plant for changes in phenotype consistent with the presumed function of the candidate homolog. Optionally, the plant into which these nucleic acids are introduced is a monocot such as from the family Gramineae. Exemplary plants include maize, sorghum, wheat, rice, canola, alfalfa, cotton, and soybean.

C. Computer Modeling

The present invention provides a process of modeling/analyzing data representative of the sequence a polynucleotide or polypeptide of the present invention. The process comprises entering sequence data of a polynucleotide or polypeptide of the present invention into a machine, manipulating the data to model or analyze the structure or activity of the polynucleotide or polypeptide, and displaying the results of the modeling or analysis. A variety of modeling and analytic tools are well known in the art and available from such commercial vendors as Genetics Computer Group (Version 10, Madison, Wis.). Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a T1 ribonuclease digestion of a polynucleotide of the present invention; 4) identify PCR primers with minimal self-complementarity; 5) compare two protein or nucleic acid sequences and identifying points of similarity or dissimilarity between them; 6) compute pairwise distances between sequences in an alignment, reconstruct phylogentic trees using distance methods, and calculate the degree of divergence of two protein coding regions; 7) identify patterns such as coding regions, terminators, repeats, and other consensus patterns in polynucleotides of the present invention; 8) identify RNA secondary structure; 9) identify sequence motifs, isoelectric point, secondary structure, hydrophobicity, and antigenicity in polypeptides of the present invention; and, 10) translate polynucleotides of the present invention and backtranslate polypeptides of the present invention.

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result. Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays.

Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling the nucleic acids of the present invention is readily achieved such as by the use of labeled PCR primers.

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries.

Total RNA Isolation

The RNA for SEQ ID NO: 1 was isolated from maize line B73 night harvested ear shoot tissue, including the husk, at the V-12 stage. Total RNA was isolated from maize tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162: 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATtract system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first strand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C. Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight. After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A Laboratory Manual, 2$^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize sequence database.
4. A Sal-A20 oligo nucleotide: TCG ACC CAC GCG TCC GM AAA AAA AAA AAA AAA AAA, listed in SEQ ID NO: 3, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search. Gene identities were determined by conducting BLAST (Basic Local Alignment Search Tool; Altschul, S. F., et al., (1990) J. Mol. Biol. 215:403–410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272, 1993) provided by the NCBI. In some cases, the sequencing data from two or more clones containing overlapping segments of DNA were used to construct contiguous DNA sequences.

EXAMPLE 4

This example shows the relevant features and domains of the Rad3 polypeptide of SEQ ID NO: 2. The key to features and domains is shown at the end of this example.

```
Amino Acid Sequence of RAD3 Orthologue-1 (SEQ ID NO:2)

1 MRFDLDGLPV HFPYAAIYPE QHAYMGELKR ALDARGHALL EMPTGTGKTA

51 ALISLITSYS LANPARPLRL IYCTRTVHEM EKTLAELRLL FAHLPPAASR

101 SLLALGLSSR KNLCIHPQAS AAAARDSVDT ACRRLTASWV REKASSDPDS

151 TPLCELYETF DRAAAAGDLA SFMPPGVYTL ADLRALGRER RVCPYFLARQ

201 MVKYANVVVY SYQYLLDPKV ASIVSREMQK ECVVVFDEAH NIDNVCIEAL

251 SVSIRKQTLE GAERNLRRIS QEIDRFKATD ANRLRAEYNR LVDGLAQRGN

301 LPISDAWLAN PSLPDDILKE AVPGNIRRAE HFLAVLRRLV RFLDGRLETE

351 NVENEMPVSF VASIHSQAGI DQKMLRFCYD RLHSLMMTLE ITDTDEFMHI

401 QTICDFATLI GTYTRGFSII IEPYDDRMPD IRDPVIQLSW HDASLAIRPV

451 FDRFETVVIT SGTLSPIDLY PRLLNFNPVI SRSFTMSLTR DCICPMVLTR

501 GSDQLPVSTK FDMRSDPGVV RNYGRLLLEM ASAVPDGIVC FFVSYSYMDG

551 IVNSWHEMGI LQDIMQHKLV FIETPDVVET TLALDNYRKA CDCGRGAIFF

601 SVARGKVAEG IDFDRHYGRL VIMFGVPFQY TLSRILLARL EYLRETFQIK

651 EGDFLTFDAL RQAAQCVGRV IRSKADYGMM IFADKRYSRH DKRSKLPGWI

701 LSHLHDAHLN LSTDMALHIA REFLRRMAQP YDKAGSGGKK TLLTEEDLEN

751 LAQDGMAM*
```

The ATP binding domain is underlined and the active site Lys identified in bold (K). The DEAH and GRG motifs common to DNA dependent ATPase/helicase family are highlighted. Amino acids considered to be important to the activity level of the Rad3 protein are shown in bold italics.

EXAMPLE 5

This example provides methods of plant transformation and regeneration using the polynucleotides of the present invention, as well as a method to determine their effect on transformation efficiency.

A. Maize Transformation by Particle Bombardment.

Transformation of a Rad3 construct along with a marker-expression cassette (for example, UBI::moPAT-GFPm:: pinII) into genotype Hi-II follows a well-established bombardment transformation protocol used for introducing DNA into the scutellum of immature maize embryos (Songstad, D. D. et al., In Vitro *Cell Dev. Biol. Plant* 32:179–183, 1996). It is noted that any suitable method of transformation can be used, such as *Agrobacterium*-mediated transformation and many other methods. To prepare suitable target tissue for transformation, ears are surface sterilized in 50% Chlorox bleach plus 0.5% Micro detergent for 20 minutes, and rinsed two times with sterile water. The immature embryos (approximately 1–1.5 mm in length) are excised and placed embryo axis side down (scutellum side up), 25 embryos per plate. These are cultured onto medium containing N6 salts, Erikkson's vitamins, 0,69 g/l proline, 2 mg/l 2,4-D and 3% sucrose. After 4–5 days of incubation in the dark at 28° C., embryos are removed from the first medium and cultured onto similar medium containing 12% sucrose. Embryos are allowed to acclimate to this medium for 3 h prior to transformation. The scutellar surface of the immature embryos is targeted using particle bombardment. Embryos are transformed using the PDS-1000 Helium Gun from Bio-Rad at one shot per sample using 650PSI rupture disks. DNA delivered per shot averages approximately 0.1667 μg. Following bombardment, all embryos are maintained on standard maize culture medium (N6 salts, Erikkson's vitamins, 0.69 g/l proline, 2 mg/l 2,4-D, 3% sucrose) for 2–3 days and then transferred to N6-based medium containing 3 mg/L Bialaphos®. Plates are maintained at 28° C. in the dark and are observed for colony recovery with transfers to fresh medium every two to three weeks. After approximately 10 weeks of selection, selection-resistant GFP positive callus clones can be sampled for presence of Rad3 mRNA and/or protein. Positive lines are transferred to 288J medium, an MS-based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developing plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Plants are monitored for expression of Rad3 mRNA and/or protein. Recovered colonies and plants are scored based on GFP visual expression, leaf painting sensitivity to a 1% application of Ignite® herbicide, and molecular characterization via PCR and Southern analysis.

B. Soybean Transformation by Particle Bombardment

Soybean embryos are bombarded with a plasmid containing a Rad3 nucleotide sequence encoding a protein of the present invention operably linked to a selected promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188), and the 3' region of the nopaline synthase gene from the T-DNA of the Ti plasmid of Agrobacterium tumefaciens. The expression cassette comprising the nucleotide sequence encoding a protein of the present invention operably linked to the selected promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

C. Maize Transformation by Agrobacterium

Transformation of a Rad3 cassette along with UBI::moPAT~moGFP::pinII into a maize genotype such as Hi-II (or inbreds such as Pioneer Hi-Bred International, Inc. proprietary inbreds N46 and P38) is also done using the Agrobacterium mediated DNA delivery method, as described by U.S. Pat. No. 5,981,840 with the following modifications. Again, it is noted that any suitable method of transformation can be used, such as particle-mediated transformation, as well as many other methods. Agrobacterium cultures are grown to log phase in liquid minimal-A medium containing 100 µM spectinomycin. Embryos are immersed in a log phase suspension of Agrobacteria adjusted to obtain an effective concentration of 5×10$^8$ cfu/ml. Embryos are infected for 5 minutes and then co-cultured on culture medium containing acetosyringone for 7 days at 20° C. in the dark. After 7 days, the embryos are transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with 3 mg/L Bialaphos® as the selective agent. Plates are maintained at 28° C. in the dark and are observed for colony recovery with transfers to fresh medium every two to three weeks. Positive lines are transferred to an MS-based medium with lower sucrose and hormone levels, to initiate plant regeneration. Following somatic embryo maturation (2–4 weeks), well-developed somatic embryos are transferred to medium for germination and transferred to the lighted culture room. Approximately 7–10 days later, developed plantlets are transferred to medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to Classic™ 600 pots (1.6 gallon) and grown to maturity. Recovered colonies and plants are scored based on GFP visual expression, leaf painting sensitivity to a 1% application of Ignite® herbicide, and molecular characterization via PCR and Southern analysis.

D. Determining Changes in Transformation Efficiency

It is expected that transformation frequency of any target will be improved by introducing Rad3 using Agrobacterium or particle bombardment This example will only describe the comparison to detect increased transformation efficiency in maize. One of skill in the art will see the obvious extension to testing transformation efficiency in other target organisms, including plants such as soybean. Plasmids described in this example are used to transform Hi-II immature embryos using particle delivery or the *Agrobacterium*. The effect of Rad3 can be measured by comparing the transformation efficiency of Rad3 constructs co-transformed with GFP constructs to the transformation efficiency of control GFP constructs only. For maize, source tissue from individual ears will be split between the two test groups in order to minimize any effect on transformation efficiency due differences in starting material. Bialaphos resistant GFP+ colonies are counted using a GFP microscope and transformation frequencies are determined (percentage of initial target embryos from which at least one GFP-expressing, bialaphos-resistant multicellular transformed event grows). In both particle gun experiments and *Agrobacterium* experiments, transformation frequencies are expected to be greatly increased in the Rad3 treatment group.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated polypeptide comprising an amino acid sequence having at least 90% sequence identity over the entire length of SEQ ID NO: 2, as determined by the GAP algorithm under default parameters, wherein said polypeptide has pyrimidine dimer excision activity.

2. The isolated polypeptide of claim 1, wherein the amino acid sequence has at least 95% sequence identity to SEQ ID NO: 2.

3. The isolated polypeptide of claim 1, wherein the polypeptide is SEQ ID NO: 2.

4. An isolated polypeptide encoded by a nucleic acid sequence having at least 90% sequence identity over the entire length of SEQ ID NO: 1, as determined by the GAP algorithm under default parameters, wherein the encoded polypeptide has pyrimidine dimer excision activity.

5. The isolated polypeptide of claim 4, wherein the nucleic acid sequence has at least 95% sequence identity to SEQ ID NO: 1.

6. An isolated polypeptide encoded by SEQ ID NO: 1.

* * * * *

SEQUENCE LISTING

```
<160> NUMBER OF SEQ ID NOS: 3

<210> SEQ ID NO 1
<211> LENGTH: 2553
<212> TYPE: DNA
<213> ORGANISM: Zea mays
<220> FEATURE:
<221> NAME/KEY: CDS
<222> LOCATION: (148)...(2421)

<400> SEQUENCE: 1
gacccacgcg tccggggca ttccaccgag cacctcacgt gatctccacc ccgcggcggc      60
ggcgcgagca ccgtctccgc ctctccgctc tccggcgaat caaaccccct cggcgttgcc    120
cctcggttgc ctttcccctc cgccaca atg cgg ttt gac ctg gat ggc ctg ccc   174
                                Met Arg Phe Asp Leu Asp Gly Leu Pro
                                  1               5 gtg cac ttc ccg tac gcg gcg atc tac ccg gag cag cac gcg tac atg   222
Val His Phe Pro Tyr Ala Ala Ile Tyr Pro Glu Gln His Ala Tyr Met
 10              15                  20                  25 ggg gag ctc aag cgc gcc ctc gac gcg cgc ggg cac gcg ctc ctc gag   270
Gly Glu Leu Lys Arg Ala Leu Asp Ala Arg Gly His Ala Leu Leu Glu
                 30                  35                  40 atg ccc acg ggc acc ggc aag acg gcg gcg ctc atc tcc ctc atc acc   318
Met Pro Thr Gly Thr Gly Lys Thr Ala Ala Leu Ile Ser Leu Ile Thr
             45                  50                  55 tcc tac tcc ctc gcc aac ccg gcc cgc ccg ctc cgc ctc atc tat tgc   366
Ser Tyr Ser Leu Ala Asn Pro Ala Arg Pro Leu Arg Leu Ile Tyr Cys
         60                  65                  70 acc cgc acc gtg cac gag atg gag aag acc ctc gcc gag ctc cgc ctc   414
Thr Arg Thr Val His Glu Met Glu Lys Thr Leu Ala Glu Leu Arg Leu
     75                  80                  85 ctc ttc gcc cac ctc ccg ccc gcg gcc tcc cgc tcc ctc ctc gcg ctc   462
Leu Phe Ala His Leu Pro Pro Ala Ala Ser Arg Ser Leu Leu Ala Leu
 90                  95                 100                 105 ggc ctc tcc tcc cgc aag aac ctc tgc atc cac ccg cag gcg tcc gcc   510
Gly Leu Ser Ser Arg Lys Asn Leu Cys Ile His Pro Gln Ala Ser Ala
                110                 115                 120 gcc gcc gcc cgg gac tcc gtc gac acc gcc tgc cgc cgc ctt acg gcc   558
Ala Ala Ala Arg Asp Ser Val Asp Thr Ala Cys Arg Arg Leu Thr Ala
            125                 130                 135 tcc tgg gtc cgc gag aag gcc tcc tcc gac ccg gac tcc acc ccg ctg   606
Ser Trp Val Arg Glu Lys Ala Ser Ser Asp Pro Asp Ser Thr Pro Leu
        140                 145                 150 tgc gag tta tac gag acg ttc gac cgg gcc gct gcc gcc ggc gac ctc   654
Cys Glu Leu Tyr Glu Thr Phe Asp Arg Ala Ala Ala Ala Gly Asp Leu
    155                 160                 165
```

-continued

| | |
|---|---|
| gcc tcc ttc atg ccg ccc ggg gtg tac acc ctg gca gac ctc cgc gcg<br>Ala Ser Phe Met Pro Pro Gly Val Tyr Thr Leu Ala Asp Leu Arg Ala<br>170                         175                   180                      185 | 702 |
| ctc gga agg gag cgc cgg gtc tgc cct tac ttc ctt gcc agg cag atg<br>Leu Gly Arg Glu Arg Arg Val Cys Pro Tyr Phe Leu Ala Arg Gln Met<br>                   190                   195                   200 | 750 |
| gtc aag tac gcc aat gtt gtg tac agc tac cag tac ctg ctc gac<br>Val Lys Tyr Ala Asn Val Val Tyr Ser Tyr Gln Tyr Leu Leu Asp<br>205                   210                  215 | 798 |
| ccc aag gtg gcc agc att gtg tcc agg gag atg cag aag gag tgt gtg<br>Pro Lys Val Ala Ser Ile Val Ser Arg Glu Met Gln Lys Glu Cys Val<br>220                         225                   230 | 846 |
| gtc gtg ttc gat gag gct cac aac att gac aat gtc tgc ata gag gcg<br>Val Val Phe Asp Glu Ala His Asn Ile Asp Asn Val Cys Ile Glu Ala<br>235                         240                   245 | 894 |
| ctg agc gtc agc atc cgc aag cag acg ctg gaa ggc gca gag cga aat<br>Leu Ser Val Ser Ile Arg Lys Gln Thr Leu Glu Gly Ala Glu Arg Asn<br>250                       255                 260               265 | 942 |
| ctg cgg cgc atc tcg caa gag atc gac agg ttc aag gcc acc gat gcc<br>Leu Arg Arg Ile Ser Gln Glu Ile Asp Arg Phe Lys Ala Thr Asp Ala<br>                   270                   275                   280 | 990 |
| aat agg ctt cgt gct gaa tac aac aga ctg gtg gat gga ctg gca cag<br>Asn Arg Leu Arg Ala Glu Tyr Asn Arg Leu Val Asp Gly Leu Ala Gln<br>                  285                   290                   295 | 1038 |
| cga gga aat cta cca ata tcg gat gct tgg ctc gcg aat ccg tct ttg<br>Arg Gly Asn Leu Pro Ile Ser Asp Ala Trp Leu Ala Asn Pro Ser Leu<br>                   300                   305                   310 | 1086 |
| cct gat gac atc ttg aag gaa gct gtt cct gga aac ata agg agg gct<br>Pro Asp Asp Ile Leu Lys Glu Ala Val Pro Gly Asn Ile Arg Arg Ala<br>315                         320                   325 | 1134 |
| gaa cat ttt ctt gct gtc ttg cgg agg ctt gtg aga ttc ctt gat ggc<br>Glu His Phe Leu Ala Val Leu Arg Arg Leu Val Arg Phe Leu Asp Gly<br>330                         335                   340               345 | 1182 |
| cgg ctt gaa aca gaa aat gtt gag aat gaa atg cca gtt tcc ttt gtt<br>Arg Leu Glu Thr Glu Asn Val Glu Asn Glu Met Pro Val Ser Phe Val<br>                   350                   355                   360 | 1230 |
| gcc tca atc cat tcc cag gct gga atc gac caa aaa atg ctg agg ttt<br>Ala Ser Ile His Ser Gln Ala Gly Ile Asp Gln Lys Met Leu Arg Phe<br>                   365                   370                   375 | 1278 |
| tgt tat gac cgg cta cac tcc cta atg atg aca tta gag ata act gat<br>Cys Tyr Asp Arg Leu His Ser Leu Met Met Thr Leu Glu Ile Thr Asp<br>380                         385                   390 | 1326 |
| aca gat gag ttc atg cac ata cag acc ata tgt gac ttt gcc aca ctg<br>Thr Asp Glu Phe Met His Ile Gln Thr Ile Cys Asp Phe Ala Thr Leu<br>395                         400                   405 | 1374 |
| att gga act tat aca cgg ggc ttt tct att ata ata gag ccg tat gat<br>Ile Gly Thr Tyr Thr Arg Gly Phe Ser Ile Ile Ile Glu Pro Tyr Asp<br>410                         415                   420               425 | 1422 |
| gat aga atg cct gat att cgt gat cct gtt att cag ctg agt tgg cat<br>Asp Arg Met Pro Asp Ile Arg Asp Pro Val Ile Gln Leu Ser Trp His<br>                   430                   435                   440 | 1470 |
| gat gct tca ctc gca ata aga cct gtt ttt gat cgt ttc gaa acc gtt<br>Asp Ala Ser Leu Ala Ile Arg Pro Val Phe Asp Arg Phe Glu Thr Val<br>                   445                   450                   455 | 1518 |
| gtg atc act tct gga act ctc agc cca ata gat ctt tac cct cgt ctc<br>Val Ile Thr Ser Gly Thr Leu Ser Pro Ile Asp Leu Tyr Pro Arg Leu<br>460                         465                   470 | 1566 |
| ttg aat ttt aat cct gtc ata agc aga agc ttc acc atg tcc tta aca<br>Leu Asn Phe Asn Pro Val Ile Ser Arg Ser Phe Thr Met Ser Leu Thr<br>475                         480                   485 | 1614 |

```
aga gat tgt att tgt ccc atg gtc ttg acc cga gga agt gat cag cta    1662
Arg Asp Cys Ile Cys Pro Met Val Leu Thr Arg Gly Ser Asp Gln Leu
490             495                 500                 505 cct gtg agt aca aag ttc gat atg cgt agt gat cct ggt gtt gtg agg    1710
Pro Val Ser Thr Lys Phe Asp Met Arg Ser Asp Pro Gly Val Val Arg
                510                 515                 520 aat tat ggc cgc ctc ttg ctg gaa atg gct tct gct gtt cca gat ggc    1758
Asn Tyr Gly Arg Leu Leu Leu Glu Met Ala Ser Ala Val Pro Asp Gly
            525                 530                 535 ata gtt tgc ttt ttt gtc agt tat tcc tat atg gat ggc att gtc aac    1806
Ile Val Cys Phe Phe Val Ser Tyr Ser Tyr Met Asp Gly Ile Val Asn
        540                 545                 550 agc tgg cac gaa atg gga att ctg cag gac atc atg caa cat aaa tta    1854
Ser Trp His Glu Met Gly Ile Leu Gln Asp Ile Met Gln His Lys Leu
555                 560                 565 gtg ttt atc gaa aca cca gat gtc gtt gag aca aca ttg gct ctt gat    1902
Val Phe Ile Glu Thr Pro Asp Val Val Glu Thr Thr Leu Ala Leu Asp
570                 575                 580                 585 aac tac aga aag gca tgt gat tgt gga aga ggt gcc att ttc ttc tct    1950
Asn Tyr Arg Lys Ala Cys Asp Cys Gly Arg Gly Ala Ile Phe Phe Ser
                590                 595                 600 gtt gcc agg ggc aaa gtt gct gaa ggt att gat ttt gat cgg cac tat    1998
Val Ala Arg Gly Lys Val Ala Glu Gly Ile Asp Phe Asp Arg His Tyr
            605                 610                 615 ggc aga tta gtt atc atg ttt ggt gtt cct ttc cag tac aca ttg agt    2046
Gly Arg Leu Val Ile Met Phe Gly Val Pro Phe Gln Tyr Thr Leu Ser
        620                 625                 630 cgg ata ttg ctt gct agg ttg gag tac ctg cgg gaa act ttt cag ata    2094
Arg Ile Leu Leu Ala Arg Leu Glu Tyr Leu Arg Glu Thr Phe Gln Ile
635                 640                 645 aag gag ggt gac ttc cta aca ttt gat gct ttg agg caa gcg gcc caa    2142
Lys Glu Gly Asp Phe Leu Thr Phe Asp Ala Leu Arg Gln Ala Ala Gln
650                 655                 660                 665 tgt gtc ggt cgt gtt att cgc tcc aaa gct gat tat ggg atg atg ata    2190
Cys Val Gly Arg Val Ile Arg Ser Lys Ala Asp Tyr Gly Met Met Ile
                670                 675                 680 ttt gct gac aag aga tac agt cgg cat gat aaa cgg tcc aag ttg cct    2238
Phe Ala Asp Lys Arg Tyr Ser Arg His Asp Lys Arg Ser Lys Leu Pro
            685                 690                 695 ggg tgg ata ctc tcg cat ttg cat gat gcg cac cta aat ctg agc act    2286
Gly Trp Ile Leu Ser His Leu His Asp Ala His Leu Asn Leu Ser Thr
        700                 705                 710 gat atg gct ctc cat ata gct cgt gag ttt ctc cgg agg atg gca cag    2334
Asp Met Ala Leu His Ile Ala Arg Glu Phe Leu Arg Arg Met Ala Gln
715                 720                 725 cca tat gac aag gcg gga agc ggt ggc aag aaa acg ctg tta acc gag    2382
Pro Tyr Asp Lys Ala Gly Ser Gly Gly Lys Lys Thr Leu Leu Thr Glu
730                 735                 740                 745 gag gat ctg gag aat ttg gcg cag gat ggc atg gcg atg taaaaaaatg     2431
Glu Asp Leu Glu Asn Leu Ala Gln Asp Gly Met Ala Met
                750                 755 agggtactgt tgtacatttc tttttgtagc cattttatgg cggtagataa cttgtttgaa   2491
gcatcggtaa tgacgtgtgg ggccaaatca ttcttaaaaa aaaaaaaaaa aaaaaaaaaa   2551
aa                                                                 2553

<210> SEQ ID NO 2
<211> LENGTH: 758
<212> TYPE: PRT
```

<213> ORGANISM: Zea mays

<400> SEQUENCE: 2

```
Met Arg Phe Asp Leu Asp Gly Leu Pro Val His Phe Pro Tyr Ala Ala
 1               5                  10                  15
Ile Tyr Pro Glu Gln His Ala Tyr Met Gly Glu Leu Lys Arg Ala Leu
                20                  25                  30
Asp Ala Arg Gly His Ala Leu Leu Glu Met Pro Thr Gly Thr Gly Lys
            35                  40                  45
Thr Ala Ala Leu Ile Ser Leu Ile Thr Ser Tyr Ser Leu Ala Asn Pro
50                  55                  60
Ala Arg Pro Leu Arg Leu Ile Tyr Cys Thr Arg Thr His Val His Glu Met
65                  70                  75                  80
Glu Lys Thr Leu Ala Glu Leu Arg Leu Leu Phe Ala His Leu Pro Pro
                85                  90                  95
Ala Ala Ser Arg Ser Leu Leu Ala Leu Gly Leu Ser Ser Arg Lys Asn
            100                 105                 110
Leu Cys Ile His Pro Gln Ala Ser Ala Ala Ala Arg Asp Ser Val
        115                 120                 125
Asp Thr Ala Cys Arg Arg Leu Thr Ala Ser Trp Val Arg Glu Lys Ala
130                 135                 140
Ser Ser Asp Pro Asp Ser Thr Pro Leu Cys Glu Leu Tyr Glu Thr Phe
145                 150                 155                 160
Asp Arg Ala Ala Ala Gly Asp Leu Ala Ser Phe Met Pro Pro Gly
                165                 170                 175
Val Tyr Thr Leu Ala Asp Leu Arg Ala Leu Gly Arg Glu Arg Arg Val
            180                 185                 190
Cys Pro Tyr Phe Leu Ala Arg Gln Met Val Lys Tyr Ala Asn Val Val
        195                 200                 205
Val Tyr Ser Tyr Gln Tyr Leu Leu Asp Pro Lys Val Ala Ser Ile Val
    210                 215                 220
Ser Arg Glu Met Gln Lys Glu Cys Val Val Phe Asp Glu Ala His
225                 230                 235                 240
Asn Ile Asp Asn Val Cys Ile Glu Ala Leu Ser Val Ser Ile Arg Lys
                245                 250                 255
Gln Thr Leu Glu Gly Ala Glu Arg Asn Leu Arg Ile Ser Gln Glu
            260                 265                 270
Ile Asp Arg Phe Lys Ala Thr Asp Ala Asn Arg Leu Arg Ala Glu Tyr
        275                 280                 285
Asn Arg Leu Val Asp Gly Leu Ala Gln Arg Gly Asn Leu Pro Ile Ser
    290                 295                 300
Asp Ala Trp Leu Ala Asn Pro Ser Leu Pro Asp Ile Leu Lys Glu
305                 310                 315                 320
Ala Val Pro Gly Asn Ile Arg Arg Ala Glu His Phe Leu Ala Val Leu
                325                 330                 335
Arg Arg Leu Val Arg Phe Leu Asp Gly Arg Leu Glu Thr Glu Asn Val
            340                 345                 350
Glu Asn Glu Met Pro Val Ser Phe Val Ala Ser Ile His Ser Gln Ala
        355                 360                 365
Gly Ile Asp Gln Lys Met Leu Arg Phe Cys Tyr Asp Arg Leu His Ser
    370                 375                 380
Leu Met Met Thr Leu Glu Ile Thr Asp Thr Asp Glu Phe Met His Ile
385                 390                 395                 400
```

```
Gln Thr Ile Cys Asp Phe Ala Thr Leu Ile Gly Thr Tyr Thr Arg Gly
                405                 410                 415

Phe Ser Ile Ile Ile Glu Pro Tyr Asp Asp Arg Met Pro Asp Ile Arg
            420                 425                 430

Asp Pro Val Ile Gln Leu Ser Trp His Asp Ala Ser Leu Ala Ile Arg
        435                 440                 445

Pro Val Phe Asp Arg Phe Glu Thr Val Ile Thr Ser Gly Thr Leu
    450                 455                 460

Ser Pro Ile Asp Leu Tyr Pro Arg Leu Leu Asn Phe Asn Pro Val Ile
465                 470                 475                 480

Ser Arg Ser Phe Thr Met Ser Leu Thr Arg Asp Cys Ile Cys Pro Met
                485                 490                 495

Val Leu Thr Arg Gly Ser Asp Gln Leu Pro Val Ser Thr Lys Phe Asp
            500                 505                 510

Met Arg Ser Asp Pro Gly Val Val Arg Asn Tyr Gly Arg Leu Leu Leu
        515                 520                 525

Glu Met Ala Ser Ala Val Pro Asp Gly Ile Val Cys Phe Phe Val Ser
    530                 535                 540

Tyr Ser Tyr Met Asp Gly Ile Val Asn Ser Trp His Glu Met Gly Ile
545                 550                 555                 560

Leu Gln Asp Ile Met Gln His Lys Leu Val Phe Ile Glu Thr Pro Asp
                565                 570                 575

Val Val Glu Thr Thr Leu Ala Leu Asp Asn Tyr Arg Lys Ala Cys Asp
            580                 585                 590

Cys Gly Arg Gly Ala Ile Phe Phe Ser Val Ala Arg Gly Lys Val Ala
        595                 600                 605

Glu Gly Ile Asp Phe Asp Arg His Tyr Gly Arg Leu Val Ile Met Phe
    610                 615                 620

Gly Val Pro Phe Gln Tyr Thr Leu Ser Arg Ile Leu Leu Ala Arg Leu
625                 630                 635                 640

Glu Tyr Leu Arg Glu Thr Phe Gln Ile Lys Glu Gly Asp Phe Leu Thr
                645                 650                 655

Phe Asp Ala Leu Arg Gln Ala Ala Gln Cys Val Gly Arg Val Ile Arg
            660                 665                 670

Ser Lys Ala Asp Tyr Gly Met Met Ile Phe Ala Asp Lys Arg Tyr Ser
        675                 680                 685

Arg His Asp Lys Arg Ser Lys Leu Pro Gly Trp Ile Leu Ser His Leu
    690                 695                 700

His Asp Ala His Leu Asn Leu Ser Thr Asp Met Ala Leu His Ile Ala
705                 710                 715                 720

Arg Glu Phe Leu Arg Arg Met Ala Gln Pro Tyr Asp Lys Ala Gly Ser
                725                 730                 735

Gly Gly Lys Lys Thr Leu Leu Thr Glu Glu Asp Leu Glu Asn Leu Ala
            740                 745                 750

Gln Asp Gly Met Ala Met
        755

<210> SEQ ID NO 3
<211> LENGTH: 36
<212> TYPE: DNA
<213> ORGANISM: Artificial Sequence
```

```
-continued

<220> FEATURE:
<223> OTHER INFORMATION: Designed oligonucleotide based upon the adapter
      sequence and poly T to remove clones which have a
      poly A tail but no cDNA.

<400> SEQUENCE: 3
tcgacccacg cgtccgaaaa aaaaaaaaaa aaaaaa                                    36
```